United States Patent [19]

Halm

[11] 4,123,268

[45] Oct. 31, 1978

[54] BORON CHELATES AS ACCEPTOR TYPE SENSITIZERS FOR PHOTOCONDUCTIVE POLYMERS

[75] Inventor: James M. Halm, Lombard, Ill.

[73] Assignee: Addressograph-Multigraph Corporation, Cleveland, Ohio

[21] Appl. No.: 808,859

[22] Filed: Jun. 22, 1977

[51] Int. Cl.² .......................... G03G 5/09; G03G 5/04
[52] U.S. Cl. .................................. 96/1 PC; 96/1.5 R; 96/1.6
[58] Field of Search .................... 96/1.5, 1.6, 1 PC

[56] References Cited

U.S. PATENT DOCUMENTS

| | | | |
|---|---|---|---|
| 3,163,530 | 12/1964 | Schlesinger | 96/1.6 |
| 3,567,439 | 3/1971 | Daniel et al. | 96/1.6 |
| 3,607,257 | 9/1971 | Johnson | 96/1.6 |
| 3,647,429 | 3/1972 | Goldman et al. | 96/1.5 |
| 3,711,280 | 1/1973 | Johnson | 96/1.6 |
| 3,719,486 | 3/1973 | Goldman et al. | 96/1.6 |
| 3,966,471 | 6/1976 | Hasegawa et al. | 96/1.5 |

*Primary Examiner*—Roland E. Martin, Jr.

[57] ABSTRACT

A series of chelated diketones in which the chelated atom is boron can be used as acceptor type sensitizers for polymeric photoconductors of the donor type used in electrophotography.

22 Claims, No Drawings

BORON CHELATES AS ACCEPTOR TYPE SENSITIZERS FOR PHOTOCONDUCTIVE POLYMERS

BACKGROUND OF THE INVENTION

This invention relates to sensitizers for use in electrophotography. In one of its more particular aspects this invention relates to the use of a class of chelated diketones as acceptor type sensitizers for polymeric photoconductors of the donor type in an electrophotographic process.

SUMMARY OF THE INVENTION

The sensitizers of this invention have the formula

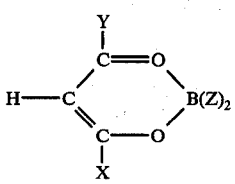

where X, Y and Z can be alkyl, aryl or an electron withdrawing group and can be the same or different.

These materials, which are chelate derivatives of 1,3-diketones have been observed to increase the sensitivity to electromagnetic radiation in the visible portion of the spectrum of polymeric photoconductors of the donor type.

DESCRIPTION OF THE PREFERRED EMBODIMENTS

The sensitizers of this invention may be incorporated with organic photoconductive polymers of the donor type, of which a wide variety are known. These include polystyrenes, polyvinylxylenes, polyvinylnaphthalenes, poly-4-vinyl biphenyl, poly-9-vinylanthracene, poly-3-vinylpyrene, poly-2-vinylquinoline, polyacenaphthalene, polyindene, polycarbonates and polyvinylcarbazole and derivatives thereof. The latter form a preferred subgroup of photoconductive polymers and will be exemplified herein.

Poly-N-vinylcarbazole, for example, is available under the trademark Luvican sold by Badische Anilin und Sodafabrik A. G., Ludwigshafen, Germany. This polymer can have a molecular weight which may vary over a wide range of about 20,000–5,000,000. The preferred molecular weight range for electrophotographic applications is from about 200,000 to 2,000,000.

The poly-N-vinylcarbazole (PVK) is dissolved in a suitable solvent such as chlorobenzene and the sensitizer added.

The sensitizer is used in an amount expressed as moles of sensitizer per 100 moles of polymer. In the case of PVK the molecular weight is taken on the basis of the molecular weight of the N-vinylcarbazole monomer which is 193.1. The preferred range is from about 1 mole to 35 moles.

Other photoconductive polymers in the preferred subgroup include the polyvinylbenzocarbazoles described in U.S. Pat. No. 3,751,246 to Helen C. Printy and Evan S. Baltazzi and the polyvinyliodobenzocarbazoles described in U.S. Pat. No. 3,764,316 to Earl E. Dailey, Jerry Barton, Ralph L. Minnis and Evan S. Baltazzi.

The sensitizer of this invention include a large number of compounds as defined by means of the structural formula given above. The following is a partial list of such sensitizers:

- difluoroboron-1,3-diphenyl-1,3-propanedionate
- difluoroboron-1-phenyl-3-methyl-1,3-propanedionate
- difluoroboron-1,3-dimethyl-1,3-propanedionate
- difluoroboron-1,3-bis(4-fluorophenyl)-1,3-propanedionate
- difluoroboron-1,3-bis(4-methoxyphenyl)-1,3-propanedionate
- difluoroboron-1,3-bis(4-trifluoromethylphenyl)-1,3-propanedionate
- difluoroboron-1-(4-fluorophenyl)-3-(4-methoxyphenyl)-1,3-propanedionate
- difluoroboron-1-trifluoromethyl-3-(2-thenyl)-1,3-propanedionate
- difluoroboron-1-(trifluoromethylphenyl-3-(4-methoxyphenyl)-1,3-propanedionate
- diphenylboron-1,3-diphenyl-1,3-propanedionate
- diphenylboron-1-phenyl-3-methyl-1,3-propanedionate
- diphenylboron-1,3-bis(4-fluorophenyl)-1,3-propanedionate
- diphenylboron-1,3-bis(4-trifluoromethylphenyl)-1,3-propanedionate
- diphenylboron-1-trifluoromethyl-3-(2-thenyl)-1,3-propanedionate The chelate sensitizers of this invention have been found to improve the photoresponse of photoconductors with which they are incorporated. Organic photoconductors are known to have a rather slow response to electromagnetic radiation in the visible range, being more sensitive to ultraviolet radiation.

In electrophotographic reproduction an electrostatic charge is applied to the photoconductor which is imaged by exposing to a pattern of light and shadow comprising electromagnetic radiation in the visible range to produce a latent electrostatic image. A developed material image is produced by the application of electroscopic powder to the latent image.

Use of the sensitizers of this invention enables the use of conventional incandescent lamps as sources of illumination in electrophotographic reproduction equipment.

A donor-acceptor charge transfer complex is formed upon combination of organic photoconductors with the sensitizers of this invention.

The improvement in photoresponse of the photoconductor depends to a large extent upon the solubility of the charge transfer complex in the solvent system employed. A wide range of solvents and solvent blends may be used depending on the particular polymer with which the sensitizer combines to form the complex. Exemplary of such solvents are toluene, acetone, methyl ethyl ketone, acetyl acetone, acetyl chloride, amyl acetate, amyl formate, benzaldehyde, butyl acetate, butyl bromide, butyl methacrylate, butyl Cellosolve, butyl stearate, butyrolactone, Cellosolve, cyclohexanone, diacetone alcohol, butyl ether, diethyl ether, dimethyl ether, dioxane, ethyl benzoate, ethyl chloride, ethylene oxide, furan, hexanediol, methyl Cellosolve. Preferred solvents are cyclohexanone and tetrahydrofuran.

The sensitizer and photoconductor may be both added to the solvent or each may be dissolved or dispersed separately and then combined.

Since the photoconductors sensitized in accordance with this invention are polymeric photoconductors, the sensitized photoconductor can be applied in the form of a polymeric film to a conductive base support in order to provide an electrophotographic recording element.

The film is applied in the form of a uniform continuous layer by conventional coating means such as a wire-wound rod, a trailing blade coater or a meniscus coater at the rate of about 0.5 gram to 4.0 grams per square foot, preferably 0.75 gram to 1.0 gram, to produce a film thickness in the range of about 2 microns to 75 microns, preferably in the range of 25 microns to 35 microns. The coating is passed through a drying oven in order to force evaporate excess solvent.

The invention will be better understood by reference to the following examples which are intended to illustrate but not to unnecessarily limit the scope of this invention which is defined in the claims appended hereto.

EXAMPLE 1

Preparation of 1,3-bis(4-fluorophenyl)-1,3-propanedione

Into a dry 500 ml. three-neck flask fitted with a condenser-drying tube combination and a dropping funnel was added 5.72 g. (0.19 mole) of sodium hydride, (50%) in oil. The resulting solid was washed three times with 30 ml. portions of petroleum ether. Dimethyl sulfoxide, DMSO, 15 ml. was added and the mixture was stirred for 1 hour. Ethyl p-fluorobenzoate, 20 g. (0.19 mole) was added and the mixture was stirred for an additional ten minutes. p-Fluoroacetophenone, 8.2 g. (0.095 mole) was dissolved in 100 ml. DMSO and the solution was added via a dropping funnel to the flask contents over a period of one hour. An exothermic reaction ensued with liberation of hydrogen and the formation of a deep orange-brown solution. The reaction mixture was stirred for 16 hours at room temperature and then poured into a beaker containing 200 ml. of 10% aqueous hydrochloric acid and 500 g. of ice. A brown-yellow solid precipitated over a period of one hour. The liquid was decanted and the solid taken up into three portions of 200 ml. quantities of ethyl ether. The ether portions were combined, washed four times with 100 ml. portions of aqueous saturated sodium bicarbonate, concentrated to about 200 ml. and placed in a freezer for 16 hours. The sticky solid was then isolated by decanting and dissolved in hot petroleum ether. The ether solution was charcoal washed, concentrated to about one-half volume and allowed to set in a freezer for 16 hours. Nine grams of 1,3-bis(4-fluorophenyl)-1,3-propanedione was isolated in about a 50% yield as a whitish light green solid, m.p. 70°–72° C.

Preparation of difluoroboron-1,3-bis(4-fluorophenyl)-1,3-propanedionate

A 4 g. (0.015 mole) portion of 1,3-bis(4-fluorophenyl)-1,3-propanedione was added to 100 ml. of dry, nitrogen saturated dimethoxyethane and 0.015 mole of boron trifluoride etherate dissolved in dimethoxyethane was added through a dropping funnel over a period of about 10 minutes. A nitrogen sweep was maintained over the solution which was controlled at mild reflux for 6 hours. The solution was cooled to room temperature and stripped to one-half volume by distillation while maintaining the nitrogen sweep. The remaining solution was added to a five-fold quantity of high boiling ligroin, which caused the precipitation of an orange-yellow solid. The mixture was placed in a freezer for 16 hours. The solid which separated was dissolved in hot ligroin solution, was charcoal washed, filtered, stripped to one-half volume and placed in a freezer for 16 hours. Difluoroboron-1,3-bis(4-fluorophenyl)-1,3-propanedionate was obtained as a yellow crystalline solid in a yield of 4.8 g., m.p. 245°–250° C., lit. 251° C.

Difluoroboron-1,3-bis(4-fluorophenyl)-1,3-propanedionate, 0.3 mole fraction and PVIBK were mixed in freshly distilled cyclohexanone/THF (60/40) in a concentration of 5–6% solids. The resulting mixture was stirred in a capped bottle for 8 hours to achieve a solubility and then filtered through a pressure filter. The filtrate was coated on opaque aluminized Mylar to a film thickness of 4.5 microns using a meniscus coater with adjustable rheostat control of coating speed.

The resulting coated Mylar film was dark adapted for 24 hours. After electrostatic charging and subsequent light exposure, measurements were made with an electrostatic voltmeter coupled to a Gould recorder. The charge acceptance, CA; photographic speed, $I_{0.3}$; $E_o$ and dark decay were measured and found to be greatly improved over those of the unsensitized PVIBK. The results are shown in Table 1.

TABLE 1

| CA v/μ | $I_{0.3}$ μJ/cm$^2$ | $E_o$ v/μ | Dark Decay v/sec. | %/sec. |
|---|---|---|---|---|
| +213 | 8.7 | +208 | 15 | 1.6 |
| −120 | 23.0 | −119 | 4 | 0.9 |
| +173 | 7.7 | +169 | 20 | 1.4 |
| +116' | 9.2 | +111 | 15 | 3.0 |

'after 10 cycles

EXAMPLE 2

The procedure of Example 1 was followed using difluoroboron-1,3-diphenyl-1,3-propanedionate as the sensitizer and various substrates and film thicknesses. The results are shown in Table 2.

| Substrate & film thickness μ | CA v/μ | $I_{0.3}$ μJ/cm$^2$ | $E_o$ v/μ | Dark Decay v/sec. | %/sec. |
|---|---|---|---|---|---|
| opaque aluminized Mylar 6.5 | — | 11 | +167 | 15 | — |
| opaque Aluminized Mylar 4.4 | +150 −116 | 14 35 | +135 −100 | 11.2 — | 1.8 — |
| opaque aluminized Mylar 5* | +128 −110 | 12 56 | +16 −12 | — — | — — |
| transparent gold Mylar 16 | +42 −6.6 | 18 126 | +35 −5.5 | 12 — | 2.0 — |

*coating was dried 4 hours at 110° C

EXAMPLE 3

The procedure of Example 1 was followed using difluoroboron-1-phenyl-3-methyl-1,3-propanedionate as the sensitizer and various substrates and film thicknesses. The results are shown in Table 3.

TABLE 3

| Substrate & film thickness μ | CA v/μ | $I_{0.3}$ μJ/cm$^2$ | $E_o$ v/μ | Dark Decay v/sec. %/sec. |
|---|---|---|---|---|
| opaque aluminized Mylar, 1.63 | +215 −225 | 69 78 | +184 −184 | non-linear slope 26$^2$ 4.0$^2$ 7.9$^3$ 1.48$^3$ |
| Opaque aluminized | +167 | 57 | +100 | " |

TABLE 3-continued

| Substrate & film thickness $\mu$ | CA v/$\mu$ | $I_{0.3}$ $\mu J/cm^2$ | $E_o$ v/$\mu$ | Dark Decay v/sec. | %/sec. |
|---|---|---|---|---|---|
| Mylar, 2.1 opaque | −179 | 90 | −100 | | |
| aluminized | +178 | 57 | +100 | " | |
| Mylar, 3.9 | −154 | 73 | −100 | | |

[2]for 5 seconds
[3]for 5 seconds

EXAMPLE 4

The procedure of Example 1 was followed using difluoroboron-1,3-dimethyl-1,3-propanedionate as the sensitizer and an opaque aluminized Mylar film with a 1.2 micron coating. The charge acceptance was +24v/$\mu$ and −22v/$\mu$ and the $E_o$ was +21.0v/$\mu$ and −21.0v/$\mu$.

EXAMPLE 5

The procedure of Example 1 was followed using 0.2 mole fraction of difluoroboron-1,3-bis(4-methoxyphenyl)-1,3-propanedionate as the sensitizer and an opaque aluminized Mylar film with a 4.8 micron coating. Methyl benzocarbazole, 0.76 g. per 2 g. PVIBK was used as a plasticizer. The charge acceptance was +165 v/$\mu$, the photographic speed was 5.6$\mu$J/cm$^2$, $E_o$ was +161 v/$\mu$ and the dark decay was 14.3 v/sec. and 1.8% sec.

EXAMPLE 6

The procedure of Example 5 was followed using difluoroboron-1.3-bis(4-trifluoromethylphenyl)-1,3-propanedionate as the sensitizer. The charge acceptance was +141 v/$\mu$, the photographic speed was 17$\mu$J/cm$^2$, $E_o$ was +135v/$\mu$ and the dark decay was 55.5 v/sec. and 9.3%/sec.

EXAMPLE 7

The procedure of Example 5 was followed using difluoroboron-1-(4-fluorophenyl)-3-(4-methoxyphenyl)-1,3-propanedionate as the sensitizer. The charge acceptance was +188 v/$\mu$, the photographic speed was 6.8$\mu$J/cm$^2$, $E_o$ was +182 v/$\mu$ and the dark decay was 33 v/sec. and 3.8%/sec.

EXAMPLE 8

The procedure of Example 1 was followed using difluoroboron-1-(2-thenyl)-3-trifluoromethyl-1,3-propanedionate as the sensitizer. The charge acceptance was +88v/$\mu$ and −88 v/$\mu$, the photographic speed was 138$\mu$J/cm$^2$ and 192$\mu$J/cm$^2$, respectively, $E_o$ was +64 v/$\mu$ and −64 v/$\mu$ and the charge decay was 21.3 v/sec. and 31.5%/sec.

EXAMPLE 9

The procedure of Example 1 was followed using diphenyl boron-1,3-diphenyl-1,3-propanedionate as the sensitizer and a coating thickness of 5.6 microns. The charge acceptance was +77 v/$\mu$ and −54v/$\mu$, the photographic speed was 38$\mu$J/cm$^2$ and 96$\mu$J/cm$^2$, respectively; $E_o$ was +72 v/$\mu$ and −52 v/$\mu$, respectively and the dark decay was 6 v/sec and 1.5%/sec.

Exposure of the coated film to 49 w. daylight fluorescence resulted in microfilm reproduction at 0.70 sec. exposure with a resolution of 67-77 line pairs per millimeter (lp/mm.) and photopic transmission of 95% based on transmission through an opaque aluminized Mylar blank as 100%.

EXAMPLE 10

The procedure of Example 9 was followed using diphenylboron-1-phenyl-3-methyl-1,3-propendionate as the sensitizier and a coating thickness of 9.3 microns. The charge acceptance was +162 v/$\mu$, the photographic speed was 223$\mu$J/cm$^2$, $E_o$ was +150 v/$\mu$ and the charge decay was 32.5 v/sec. and 11.1%/sec.

An exposure time of 4.2 sec. resulted in a resolution of 67-77 lp/mm.

EXAMPLE 11

The procedure of Example 9 was followed using diphenylboron-1,3-bis(4-fluorophenyl)-1,3-propanedionate as the sensitizer and a 4.3 micron coating. The charge acceptance was +210v/$\mu$, the photographic speed was 53$\mu$J/cm$^2$, $E_o$ was +210 v/$\mu$ and the dark decay was less than 0.1%/sec.

An exposure time of 0.7 sec. resulted in a resolution of 134 lp/mm. and a photopic transmission of 93%.

EXAMPLE 12

The procedure of Example 1 was followed using 0.2 mole fraction of diphenylboron-1,3-bis(4-trifluoromethylphenyl)-1,3-propanedionate as the sensitizer and an opaque aluminized Mylar film with a 4.3 micron coating. n-Butylbenzocarbazole, 0.76 g. per 2 g. PVIBK was used as a plasticizer. The charge acceptance was +191v/$\mu$, the photographic speed was 69$\mu$J/cm$^2$, $E_o$ was +183 v/$\mu$ and the dark decay was 33 v/sec. and 4%/sec.

EXAMPLE 13

The procedure of Example 9 was followed using diphenylboron-1-(2-thenyl)-3-trifluoromethyl-1,3-propanedionate as the sensitizer and a 2.8 micron coating. The charge acceptance was +95 v/$\mu$ and −95 v/$\mu$, the photographic speed was 42$\mu$J/$cm^2$, respectively, $E_o$ was +65 v/$\mu$ and −65 v/$\mu$ and the dark decay was 15.2 v/sec. and 6.5%/sec. for the first 2.3 sec. and 13.2 v/sec. and 5.85%/sec. thereafter.

A 2.8 sec. exposure resulted in a resolution of 110-120 lp/mm and a photopic transmission of 97%.

EXAMPLE 14

The procedure of Example 1 was followed using difluoroboron-1-(4-trifluoromethylphenyl)-3-(4-methoxyphenyl)-1,3-propanedionate as the sensitizer and N-methylbenzocarbazole, 0.8 g. per 4.0 g. PVIBK as plasticizer. The charge acceptance was +208 v/$\mu$, the photographic speed was 8.9$\mu$J/cm$^2$, $E_o$ was +200 v/$\mu$ and the dark decay was less than 2%.

Similar results were obtained using polyvinylbenzocarbazole, polyvinylcarbazole, a capolymer of n-butyl acrylate and N-vinylcarbazole and polyvinyl-n-octylbenzocarbazole instead of the polyvinyliodobenzocarbazole exemplified above.

The invention has been described with respect to a limited number of specific embodiments. However, it is intended that alternative compositions and methods can be used and it is to be understood that this invention is not to be limited except in accordance with the following claims.

I claim:

1. A method of making a reproduction comprising the steps of applying an electrostatic charge to an organic photoconductive polymer of the electron donor type sensitized with a compound of the formula:

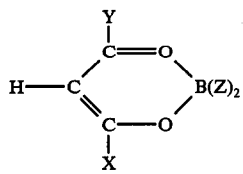

where X and Y each independently is a member selected from the group consisting of alkyl, aryl and electron withdrawing alkyl and electron withdrawing aryl and Z is a member selected from the group consisting of fluoro and phenyl, said compound being present in an amount ranging from 0.1 mole to 100 moles per 100 moles of polymer, the molecular weight of said polymer being taken as the weight of the monomer;

exposing the charged polymer to a pattern of light and shadow comprising electromagnetic radiation in the visible range to produce a latent image thereon; and applying electroscopic powder to produce a material image corresponding to said pattern of light and shadow.

2. An electrophotographic recording element comprising a conductive base support coated with an organic photoconductive polymer of the electron donor type and a sensitizer of the formula:

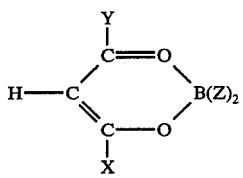

where X and Y each independently is a member selected from the group consisting of alkyl, aryl, electron withdrawing alkyl and electron withdrawing aryl and Z is a member selected from the group consisting of fluoro and phenyl.

3. An element according to claim 2 wherein the amount of sensitizer ranges from 0.1 mole to 100 moles per 100 moles of polymer, the molecular weight of said polymer being taken as the weight of the monomer.

4. An element according to claim 2 wherein the polymer is polyvinyliodobenzocarbazole.

5. An element according to claim 2 wherein the polymer is polyvinylbenzocarbazole.

6. An element according to claim 2 wherein the polymer is polyvinylcarbazole.

7. An element according to claim 2 wherein the polymer is a copolymer of n-butyl acrylate and N-vinylcarbazole.

8. An element according to claim 2 wherein the polymer is polyvinyl-n-octylbenzocarbazole.

9. An element according to claim 2 wherein the sensitizer is

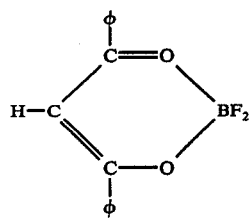

where $\phi$ is phenyl.

10. An element according to claim 2 wherein the sensitizer is

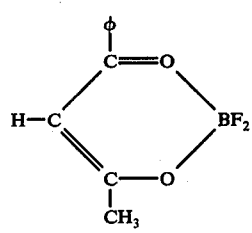

where $\phi$ is phenyl.

11. An element according to claim 2 wherein the sensitizer is

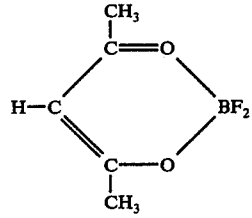

12. An element according to claim 2 wherein the sensitizer is

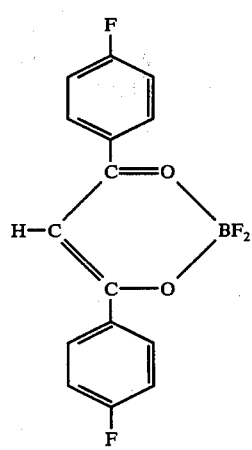

13. An element according to claim 2 wherein the sensitizer is

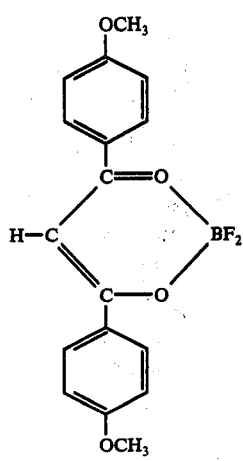

14. An element according to claim 7 wherein the sensitizer is

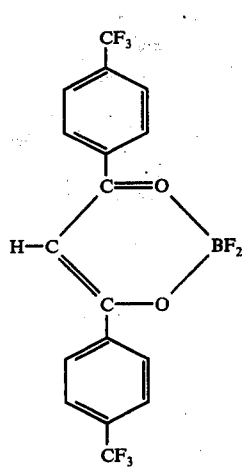

15. An element according to claim 2 wherein the sensitizer is

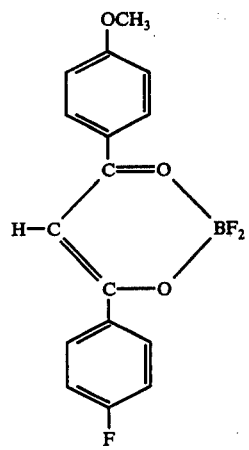

16. An element according to claim 2 wherein the sensitizer is

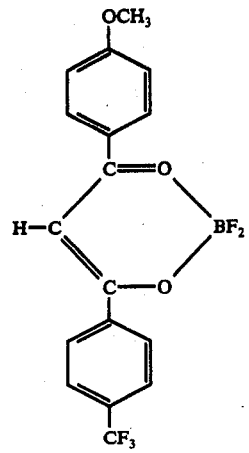

17. An element according to claim 2 wherein the sensitizer is

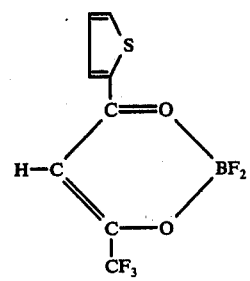

18. An element according to claim 2 wherein the sensitizer is

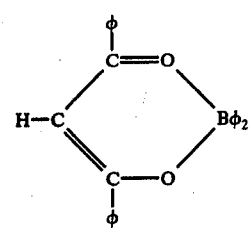

where $\phi$ is phenyl.

19. An element according to claim 2 wherein the sensitizer is

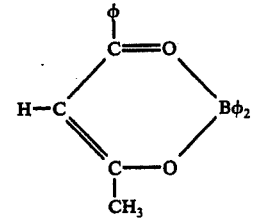

where $\phi$ is phenyl.

20. An element according to claim 2 wherein the sensitizer is

21. An element according to claim 2 wherein the sensitizer is
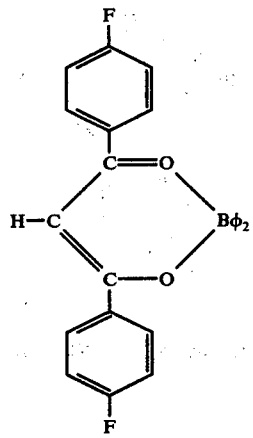
where φ is phenyl.
22. An element according to claim 2 wherein the sensitizer is
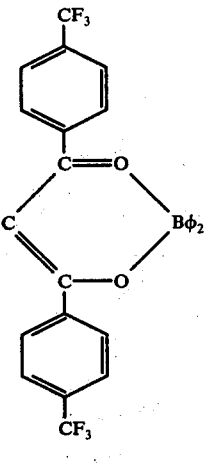
where φ is phenyl.
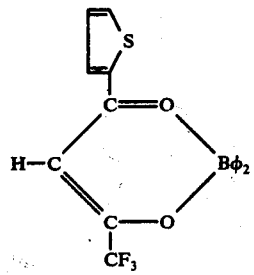
where φ is phenyl.
* * * * *